United States Patent
Miyama et al.

(10) Patent No.: US 9,656,931 B2
(45) Date of Patent: May 23, 2017

(54) CATALYST FOR ALCOHOL SYNTHESIS, APPARATUS FOR PRODUCING ALCOHOL AND METHOD FOR PRODUCING ALCOHOL

(71) Applicant: SEKISUI CHEMICAL CO., LTD., Osaka (JP)

(72) Inventors: Toshihito Miyama, Tsukuba (JP); Tomoaki Nishino, Tsukuba (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 14/649,685

(22) PCT Filed: Dec. 11, 2013

(86) PCT No.: PCT/JP2013/083183
§ 371 (c)(1),
(2) Date: Jun. 4, 2015

(87) PCT Pub. No.: WO2014/097942
PCT Pub. Date: Jun. 26, 2014

(65) Prior Publication Data
US 2015/0284306 A1    Oct. 8, 2015

(30) Foreign Application Priority Data

Dec. 20, 2012  (JP) ................. 2012-278185
Aug. 28, 2013  (JP) ................. 2013-177343

(51) Int. Cl.
| | | |
|---|---|---|
| *B01J 8/02* | (2006.01) | |
| *B01J 23/656* | (2006.01) | |
| *B01J 23/89* | (2006.01) | |
| *C07C 29/141* | (2006.01) | |
| *C07C 29/154* | (2006.01) | |
| *B01J 35/10* | (2006.01) | |
| *B01J 37/04* | (2006.01) | |
| *C07C 29/158* | (2006.01) | |
| *B01J 35/00* | (2006.01) | |
| *B01J 37/02* | (2006.01) | |
| *B01J 23/00* | (2006.01) | |
| *B01J 23/80* | (2006.01) | |
| *B01J 8/06* | (2006.01) | |
| *B01J 35/02* | (2006.01) | |

(52) U.S. Cl.
CPC ........... *C07C 29/141* (2013.01); *B01J 8/0221* (2013.01); *B01J 8/065* (2013.01); *B01J 23/002* (2013.01); *B01J 23/6562* (2013.01); *B01J 23/80* (2013.01); *B01J 23/8926* (2013.01); *B01J 23/8986* (2013.01); *B01J 35/0006* (2013.01); *B01J 37/0205* (2013.01); *B01J 37/04* (2013.01); *C07C 29/154* (2013.01); *C07C 29/158* (2013.01); *B01J 35/023* (2013.01); *B01J 35/1019* (2013.01); *B01J 35/1042* (2013.01); *B01J 35/1061* (2013.01); *B01J 37/0203* (2013.01); *B01J 37/0207* (2013.01); *B01J 2208/00415* (2013.01); *B01J 2208/00513* (2013.01); *B01J 2208/00539* (2013.01); *B01J 2208/00548* (2013.01); *B01J 2208/00893* (2013.01); *B01J 2208/025* (2013.01); *B01J 2523/00* (2013.01)

(58) Field of Classification Search
CPC ..... B01J 23/8926; C07C 29/158; C07C 31/08
USPC .......................................................... 502/241
See application file for complete search history.

(56) References Cited

U.S. PATENT DOCUMENTS

| | | | |
|---|---|---|---|
| 4,377,643 A | 3/1983 | Pesa et al. | |
| 4,751,248 A | 6/1988 | Lin et al. | |
| 2010/0298610 A1* | 11/2010 | Lysenko ................ | C07C 67/31 |
| | | | 568/484 |
| 2012/0071697 A1 | 3/2012 | Ichikawa | |

FOREIGN PATENT DOCUMENTS

| | | |
|---|---|---|
| CN | 101474565 | 7/2009 |
| CN | 102091628 | 6/2011 |
| EP | 0 021 443 | 1/1981 |
| GB | 2 171 925 | 9/1986 |
| JP | 61-500970 | 5/1986 |
| JP | 61-36730 | 8/1986 |
| JP | 61-178939 | 8/1986 |
| JP | 62-38335 | 8/1987 |
| JP | 63-162638 | 7/1988 |
| JP | 63-162639 | 7/1988 |
| JP | 64-26526 | 1/1989 |
| JP | 9-157197 | 6/1997 |
| JP | 2006-512340 | 4/2006 |
| JP | 2012-1441 | 1/2012 |
| JP | 2012-131709 | 7/2012 |
| JP | 2012-149089 | 8/2012 |
| JP | 2013/49023 | 3/2013 |
| WO | 85/03073 | 7/1985 |
| WO | 2004/056731 | 7/2004 |

OTHER PUBLICATIONS

Krishnamurthy et al., carbon monoxide adsorption and hydrogenation on Cu-Rh/SiO2, (Applied Catalysis, A: General (1994), 114(1), Abstract only).*
International Search Report issued Mar. 18, 2014 in International (PCT) Application No. PCT/JP2013/083183.
Office Action issued Mar. 2, 2016 in corresponding Chinese Application No. 201380066112.0, with English translation.
Office Action issued Oct. 31, 2016 in Chinese Application No. 201380066112.0, with English translation.
(Continued)

*Primary Examiner* — Jafar Parsa
(74) *Attorney, Agent, or Firm* — Wenderoth, Lind & Ponack, L.L.P.

(57) ABSTRACT

A catalyst for synthesizing an alcohol from a gaseous mixture comprising hydrogen and carbon monoxide, the catalyst being a mixture of catalyst particles α which convert carbon monoxide into an oxygenate, and catalyst particles β which convert an aldehyde into an alcohol.

5 Claims, 1 Drawing Sheet

(56) References Cited

OTHER PUBLICATIONS

Extended European Search Report dated Jul. 12, 2016 in European Patent Application No. 13864700.3.
Notice of Reasons for Rejection issued Sep. 27, 2016 in corresponding Japanese Application No. 2014-553092, with translation.

* cited by examiner

CATALYST FOR ALCOHOL SYNTHESIS, APPARATUS FOR PRODUCING ALCOHOL AND METHOD FOR PRODUCING ALCOHOL

TECHNICAL FIELD

The present invention relates to a catalyst for synthesizing an alcohol, an apparatus for producing an alcohol, and a method for producing an alcohol.

Priorities are claimed on Japanese Patent Application No. 2012-278185, filed Dec. 20, 2012, and Japanese Patent Application No. 2013-177343, filed Aug. 28, 2013, the contents of which are incorporated herein by reference.

BACKGROUND ART

There is ongoing progress toward widespread replacement of petroleum with bioethanol as an alternative fuel. Bioethanol is produced mainly through saccharification and fermentation of sugarcane or corn. In recent years, a technique is being developed to produce bioethanol from wood-based biomass and plant-based biomass (which are also referred to as cellulosic biomass) such as wood waste or unused portions of crops such as rice straw, which do not compete with foods and feeds.

In order to produce bioethanol from cellulosic biomass as a raw material by a conventional ethanol fermentation method, it is necessary to saccharify the cellulose. As a saccharification method, there are known a method using a concentrated sulfuric acid, a method using a diluted sulfuric acid and an enzyme, and a hydrothermal saccharification method; however, there are still many problems to be solved in order to produce bioethanol at a low cost.

Meanwhile, there is a method in which cellulosic biomass is converted to a mixed gas containing hydrogen and carbon monoxide, from which an alcohol is synthesized. With this method, an attempt is made to efficiently produce bioethanol from cellulosic biomass to which the application of alcohol fermentation is difficult. In addition, raw materials which can be used in this method are not limited to the wood-based biomass and the plant-based biomass, but also include various biomasses such as animal biomass derived from carcasses or feces of animals, garbage, waste paper and waste fiber.

Further, since a mixed gas of hydrogen and carbon monoxide is also derivable from sources other than petroleum, such as natural gas or coal, a method of synthesizing an alcohol from such a mixed gas has been studied as a technique to move away from petroleum dependency.

As a catalyst used for obtaining an oxygenate such as ethanol, acetaldehyde or acetic acid from a mixed gas of hydrogen and carbon monoxide, for example, there is known a catalyst comprising rhodium and an alkali metal which are supported on a silica gel carrier (see, for example, Patent Document 1). However, the technique of Patent Document 1 results in production of a large amount of oxygenates other than alcohols such as ethanol, whereby a long time and a large amount of energy are required for performing a step of separating alcohols.

For solving these problems, there is proposed a method for producing ethanol in which a mixed gas of carbon monoxide and hydrogen is brought into contact with a catalyst in a reaction apparatus which is filled with, at an upper layer thereof, a catalyst comprising rhodium supported on a carrier and is filled with, at a lower layer thereof, a catalyst comprising iridium and iron supported on a carrier or a catalyst comprising iridium, iron and rhodium supported on a carrier (see, for example, Patent Document 2).

PRIOR ART DOCUMENTS

Patent Documents

Patent Document 1: Japanese Examined Patent Application Publication No. Sho 61-36730
Patent Document 2: Japanese Examined Patent Application Publication No. Sho 62-38335

DISCLOSURE OF INVENTION

Problems to be Solved by the Invention

However, in the case of the invention of Patent Document 2, the ratio of alcohols in the oxygenates produced can be increased, whereas the efficiency in the oxygenate synthesis decreases at an early stage to thereby lower the production efficiency of alcohols.

The purpose of the present invention, in view of the above, is to provide a catalyst for synthesizing an alcohol, which enables the production of an alcohol with higher production efficiency over a long period of time.

Means to Solve the Problems

An alcohol synthesis catalyst of the present invention is a catalyst for synthesizing an alcohol from a gaseous mixture comprising hydrogen and carbon monoxide, and is a mixture of catalyst particles α which convert carbon monoxide into an oxygenate, and catalyst particles β which convert an aldehyde into an alcohol.

In the catalyst of the present invention, it is preferred that the volume ratio in terms of [catalyst particles β prior to mixing]/[catalyst particles α prior to mixing] is 1 or more, and that the catalyst particles α comprises rhodium and the catalyst particles β comprises copper.

An alcohol production apparatus of the present invention comprises: a reaction tube filled with the alcohol synthesis catalyst of the present invention; a supply means for supplying the gaseous mixture into the reaction tube; and a withdrawal means for withdrawing a reaction product from the reaction tube.

An alcohol production method of the present invention comprises contacting a gaseous mixture comprising hydrogen and carbon monoxide with the alcohol synthesis catalyst of the present invention to produce an alcohol.

In the present specification and claims, the term "oxygenate" denotes a molecule composed of a carbon atom, a hydrogen atom and an oxygen atom, such as alcohols (e.g., methanol, ethanol and propanol), carboxylic acids (e.g., acetic acid), aldehydes (e.g., acetaldehyde), esters (e.g., methyl formate, ethyl formate, methyl acetate and ethyl acetate). Among oxygenates, those which have 2 carbon atoms (such as acetic acid, ethanol and acetaldehyde) are referred to as "C2 oxygenate".

Effect of the Invention

By the alcohol synthesis catalyst of the present invention, an alcohol can be produced with higher production efficiency over a long period of time.

EMBODIMENTS FOR CARRYING OUT THE INVENTION (Alcohol Synthesis Catalyst)

The alcohol synthesis catalyst of the present invention (hereinafter, sometimes referred to as "synthesis catalyst") is a mixture of catalyst particles α which convert carbon monoxide into an oxygenate, and catalyst particles β which convert an aldehyde into an alcohol. By the use of a mixture of catalyst particles α and catalyst particles β as a synthesizing catalyst, an alcohol can be produced from a gaseous mixture comprising hydrogen and carbon monoxide (hereinafter, sometimes referred to simply as "gaseous mixture") with higher production efficiency for over a long period of time.

<Catalyst Particles α>

The catalyst particles α convert carbon monoxide into oxygenates and contain a hydrogenation active metal (hereinafter, the hydrogenation active metal used in the catalyst particles α is sometimes referred to the "hydrogenation active metal α"). As the catalyst particles α, it is preferable to use those which exhibit high CO conversion and high alcohol selectivity. By the use of such catalyst particles α, the production efficiency of an alcohol can be further improved.

In the present specification, the "CO conversion" is a molar percentage of CO consumed for oxygenate synthesis relative to the total CO in the gaseous mixture.

Further, the term "selectivity" means a molar percentage of the C (carbon) converted to a specific oxygenate relative to the consumed CO in the gaseous mixture. For example, according to the following formula (i), the selectivity for ethanol as an alcohol is 100 mol %. On the other hand, according to the following formula (ii), the selectivity for ethanol as a C2 oxygenate is 50 mol % and the selectivity for acetaldehyde as a C2 oxygenate is also 50 mol %. In addition, in both of the formulae (i) and (ii), the selectivity for C2 oxygenates is 100 mol %.

$$4H_2 + 2CO \rightarrow CH_3CH_2OH + H_2O \quad (i)$$

$$7H_2 + 4CO \rightarrow C_2H_5OH + CH_3CHO + 2H_2O \quad (ii)$$

As the hydrogenation active metal α, any metals conventionally known as being capable of synthesizing an oxygenate from the gaseous mixture can be used, and examples thereof include alkali metals such as lithium and sodium; elements belonging to group 7 of the periodic table, such as manganese and rhenium; elements belonging to group 8 of the periodic table, such as ruthenium; elements belonging to group 9 of the periodic table, such as cobalt and rhodium; and elements belonging to group 10 of the periodic table, such as nickel and palladium.

These hydrogenation active metals α may be used alone or in any combination of two or more thereof. As the hydrogenation active metal α, from the viewpoint of further improving the CO conversion and the alcohol selectivity, it is preferable to use a combination of rhodium, manganese and lithium, a combination of ruthenium, rhenium and sodium, or a combination of rhodium or ruthenium with an alkali metal and other hydrogenation active metal α.

The catalyst particles α may further comprise an auxiliary active metal (hereinafter, the auxiliary active metal used in the catalyst particles α is sometimes referred to "auxiliary active metal α") in addition to the hydrogenation active metal α.

Examples of the auxiliary active metal α include one or more metals selected from the group consisting of titanium, vanadium, chromium, boron, magnesium, lanthanide, and an element belonging to group 13 of the periodic table. Of these, titanium, magnesium, and vanadium are preferable, and titanium is more preferable. When the catalyst particles α contain such an auxiliary active metal α, the CO conversion and the alcohol selectivity can be further improved.

Hereinafter, the hydrogenation active metal α and the auxiliary active metal α are sometimes collectively referred to as "catalyst metal α".

As the catalyst particles α, for example, it is preferable to use one containing rhodium, it is more preferable to use one containing rhodium, manganese and an alkali metal, and it is more preferable to use one containing rhodium, manganese, an alkali metal and the auxiliary active metal α.

The catalyst particles α may be either in the form of an aggregate of the catalyst metal α or in the form of a supported catalyst in which the catalyst metal α is supported on a carrier. It is especially preferable to use the catalyst particles α in the form of a supported catalyst. By the use of a supported catalyst, the catalyst metal α can be more efficiently contacted with the gaseous mixture so that the CO conversion can be further improved.

As the carrier, any of the known carriers used for catalysts can be used and, for example, porous carriers are preferable.

There is no particular limitation with respect to the material of the porous carrier, and examples thereof include silica, zirconia, titania, magnesia, alumina, activated carbon and zeolite. Among these, silica is preferable because various silica products differing in specific surface area and pore size are commercially available.

The size of the porous carrier is not particularly limited. For example, in the case of a porous silica carrier, the particle size of the carrier is preferably in the range from 0.5 to 5,000 μm. The particle size of the porous carrier can be controlled by sifting.

In addition, it is preferred to use a porous carrier having a particle size distribution as narrow as possible.

The total of the volume of the pores of the porous carrier (total pore volume) is not particularly limited and, for example, is preferably 0.01 to 1.0 mL/g, more preferably 0.1 to 0.8 mL/g, and still more preferably 0.3 to 0.7 mL/g. When the total pore volume is below the above-mentioned lower limit, the specific surface area of the porous carrier becomes too small. As a result, there is a danger that the dispersibility of the catalyst particles α becomes low as a result of supporting the catalyst metal α, thereby lowering the CO conversion. When the total pore volume exceeds the above-mentioned upper limit, the pore diameters are too small so that the catalyst metal α hardly gets into the inside of the carrier in the process of supporting the catalyst metal α on the carrier. As a result, there is a danger that the surface area of the carrier cannot be sufficiently utilized or diffusion of the gaseous mixture into the carrier becomes difficult, so that sufficient contact between the catalyst metal α and the gaseous mixture is hindered, thereby lowering the CO conversion and the alcohol selectivity.

The total pore volume is a value measured by the aqueous titration method. In the aqueous titration method, water molecules are adsorbed onto a surface of the porous carrier, and the pore distribution is measured based on the condensation of the molecules.

The average pore diameter of the porous carrier is not particularly limited, and, for example, is preferably 0.01 to 20 nm, more preferably 0.1 to 8 nm. When the average pore diameter is below the above-mentioned lower limit, the catalyst metal α hardly gets into the inside of the carrier in the process of supporting the catalyst metal α on the carrier. As a result, there is a danger that the surface area of the carrier cannot be sufficiently utilized or the diffusion of the gaseous mixture into the carrier becomes difficult, so that sufficient contact between the catalyst metal α and the gaseous mixture is hindered, thereby lowering the CO conversion and the alcohol selectivity. When the average pore diameter exceeds the above-mentioned upper limit, the specific surface area of the porous carrier is too small. As a result, there is a danger that the catalyst metal α is poorly dispersed in the process of supporting the catalyst particles α on the carrier, thereby lowering the CO conversion.

The average pore diameter is a value measured by the following method. When the average pore diameter is at least as large as 0.1 nm, but is less than 10 nm, the average pore diameter is calculated from the total pore volume and the BET specific surface area. When the average pore diameter is at least as large as 10 nm, the average pore diameter is measured by the mercury penetration method using a porosimeter.

Here, the total pore volume is a value measured by the aqueous titration method, and the BET specific surface area is a value calculated from an adsorbed amount of nitrogen that is an adsorption gas, and a pressure at the time of adsorption.

In the mercury penetration method, a pressure is applied to inject mercury into pores of the porous carrier, and the average pore diameter is calculated from the pressure and an amount of the mercury injected.

The specific surface area of the porous carrier is not particularly limited and, for example, is preferably 1 to 1,000 $m^2/g$, more preferably 300 to 800 $m^2/g$, still more preferably 400 to 700 $m^2/g$. When the specific surface area is below the above-mentioned lower limit, the specific surface area of the porous carrier is too small. As a result, there is a danger that the catalyst metal α is poorly dispersed in the process of supporting the catalyst particles α on the carrier, thereby lowering the CO conversion. When the specific surface area exceeds the above-mentioned upper limit, the pore diameter becomes too small as a result of supporting the catalyst metal α on the carrier so that the catalyst metal α hardly gets into the inside of the carrier. As a result, there is a danger that the surface area of the carrier cannot be sufficiently utilized or the diffusion of the gaseous mixture into the carrier becomes difficult, so that sufficient contact between the catalyst metal α and the gaseous mixture is hindered, thereby lowering the CO conversion and the alcohol selectivity.

The specific surface area means the BET specific surface area, which is measured by the BET gas adsorption method using nitrogen as an adsorption gas.

When the catalyst particles α are in the form of a supported catalyst, the average particle diameter of the catalyst particles α can be determined in view of the type of the support and the like, and, for example, the average particle diameter is preferably 0.5 to 5,000 μm. When the average particle diameter of the catalyst particles α is below the above-mentioned lower limit, there is a danger that the pressure loss is large so that the flow of the gaseous mixture is hindered. When the average particle diameter of the catalyst particles α is above the above-mentioned upper limit, there is a danger that the filling density of the synthesis catalyst is small so that the efficiency of contact between the gaseous mixture and the catalyst particles α is lowered. Further, with respect to the catalyst particles α, the catalyst particles of small sizes may be compressed in the presence of a binder to form secondary particles, or the particle size may be adjusted appropriately by, for example, pulverizing the catalyst particles of large sizes.

With respect to the state of support of the catalyst metal α in the supported catalyst, there is no particular limitation. For example, the catalyst metal α may be supported in a state where the metal in the form of a powder is supported by a porous carrier, or may be supported in a state where the metal in the form of an elemental metal is supported by a porous carrier. Of these, it is preferred that the catalyst metal α is supported in a state where the metal in the form of an elemental metal is supported by a porous carrier. When the catalyst metal α is supported in a state where the metal in the form of an elemental metal is supported by a porous carrier, a large area of contact with the gaseous mixture is secured so that the CO conversion can be further improved.

The amount of the hydrogenation active metal α supported in the supported catalyst may be determined in view of the type of the hydrogenation active metal α, the type of the porous carrier and the like. For example, when silica is used as the porous carrier, the amount of the hydrogenation active metal α supported in the supported catalyst is preferably 0.05 to 30 parts by weight and more preferably 1 to 10 parts by weight, relative to 100 parts by weight of the porous carrier. When the amount is below the above-mentioned lower limit, there is a danger that the content of the hydrogenation active metal α is too low so that the CO conversion is lowered. When the amount exceeds the above-mentioned upper limit, there is a danger that the hydrogenation active metal α cannot be uniformly and highly dispersed so that the CO conversion is lowered.

The amount of the auxiliary active metal α supported in the supported catalyst may be determined in view of the type of the auxiliary active metal α, the type of the hydrogenation active metal α and the like. The amount of the auxiliary active metal α supported in the supported catalyst is preferably 0.01 to 20 parts by weight and more preferably 0.1 to 10 parts by weight, relative to 100 parts by weight of the porous carrier. When the amount is below the above-mentioned lower limit, the amount of the supported auxiliary active metal α is too small so that the achievement of effect by the auxiliary active metal α becomes difficult. When the amount is above the above-mentioned upper limit, there is a danger that the surface of the porous carrier is excessively covered by the auxiliary active metal α so that the CO conversion and/or the selectivity for an alcohol is lowered.

The amount of the catalyst metal α supported in the supported catalyst may be determined in view of the composition of the catalyst metal α, the material of the porous carrier and the like. For example, the amount of the catalyst metal α supported in the supported catalyst is preferably 0.05 to 30 parts by weight and more preferably 0.1 to 10 parts by weight, relative to 100 parts by weight of the porous carrier. When the amount is below the above-mentioned lower limit, there is a danger that the content of the supported catalyst metal α is too low so that the CO conversion is lowered. When the amount exceeds the above-mentioned upper limit, there is a danger that the catalyst metal α cannot be uniformly and highly dispersed so that the CO conversion and/or the selectivity for an alcohol is lowered.

When the catalyst particles α are in the form of a supported catalyst and contains rhodium, manganese, an alkali metal and an auxiliary active metal α, it is preferred that the catalyst has a composition represented by the following formula (I):

$$aA \cdot bB \cdot cC \cdot dD \qquad (I)$$

wherein A represents rhodium, B represents manganese, C represents an alkali metal, D represents an auxiliary active metal, a, b, c and d represent molar ratios, and a+b+c+d=1.

When D (auxiliary active metal) is titanium, a in formula (I) is preferably 0.053 to 0.98, more preferably 0.24 to 0.8, and still more preferably 0.32 to 0.67. When the value of a is below the above-mentioned lower limit, the content of rhodium is too low so that the CO conversion may not be sufficiently improved. When the value of a exceeds the above-mentioned upper limit, the content of other metals is too low so that the CO conversion may not be sufficiently improved.

When D (auxiliary active metal) is titanium, b in formula (I) is preferably 0.0006 to 0.67, more preferably 0.033 to 0.57, and still more preferably 0.089 to 0.44. When the value of b is below the above-mentioned lower limit, the content of manganese is too low so that the CO conversion may not be sufficiently improved. When the value of b exceeds the above-mentioned upper limit, the content of other metals is too low so that the CO conversion may not be sufficiently improved.

When D (auxiliary active metal) is titanium, c in formula (I) is preferably 0.00056 to 0.51, more preferably 0.026 to 0.42, and still more preferably 0.075 to 0.33. When the value of c is below the above-mentioned lower limit, the content of alkali metal is too low so that the CO conversion may not be sufficiently improved. When the value of c exceeds the above-mentioned upper limit, the content of other metals is too low so that the CO conversion may not be sufficiently improved.

When D (auxiliary active metal) is titanium, d in formula (I) is preferably 0.0026 to 0.94, more preferably 0.02 to 0.48, and still more preferably 0.039 to 0.25. When the value of d is below the above-mentioned lower limit, the content of auxiliary active metal is too low so that the CO conversion may not be sufficiently improved. When the value of d exceeds the above-mentioned upper limit, the content of other metals is too low so that the CO conversion may not be sufficiently improved.

The content of the catalyst particles α in the synthesis catalyst may be determined in view of the performance of the catalyst particles α and the like and, for example, can be appropriately determined within the range 9 to 91% by mass.

The synthesis catalyst may contain one type of the catalyst particles α or two or more types of the catalyst particles α.

The catalyst particles α can be produced by any of the conventionally known methods for producing metal catalysts. Examples of the method of producing the catalyst particles α include impregnation, immersion, ion exchange, coprecipitation and kneading, of which the impregnation is preferred. When the impregnation is used, the catalyst metal α can be more evenly dispersed in the resultant catalyst, whereby the efficiency of contact between the catalyst metal α and the gaseous mixture is increased and, hence, the CO conversion can be further improved.

Examples of raw material compounds for the catalyst metal α used for preparing the catalyst include oxides; chlorides; inorganic salts such as nitrates and carbonates; organic salts or chelate compounds such as oxalates, acetylacetonate salts, dimethylglyoxime salts and ethylenediamine acetic acid salts; carbonyl compounds; cyclopentadienyl compounds; amine complexes; alkoxide compounds; and alkyl compounds, which are generally used as the compounds for preparing metal catalysts.

An example of method of producing the catalyst particles α by the impregnation will be described below. First, the raw material compound(s) of the catalyst metal α is dissolved in a solvent such as water, methanol, ethanol, tetrahydrofuran, dioxane, hexane, benzene or toluene, and a carrier is, for example, immersed in the obtained solution (impregnation solution), thereby attaching the impregnation solution to the carrier. When a porous material is used as the carrier, after the impregnation solution sufficiently permeates the pores, the solvent is evaporated to obtain a catalyst.

Examples of the method of impregnating the carrier with the impregnation solution include a method (simultaneous method) of impregnating the carrier with a solution in which all raw material compounds have been dissolved, a method (sequential method) in which respective solutions of the raw material compounds are prepared and the carrier is sequentially impregnated with the solutions. Of these methods, the sequential method is preferred. By the use of the catalyst prepared by the sequential method, the CO conversion can be further improved and an alcohol can be produced with higher selectivity.

Examples of the sequential method include a method in which the porous carrier is impregnated with a solution (primary impregnating solution) containing the auxiliary active metal α (primary impregnation step), the porous carrier is then dried to obtain a primary support body in which the auxiliary active metal α has been supported on the porous carrier (primary support step), the primary support body is subsequently impregnated with a solution (secondary impregnating solution) containing the hydrogenation active metal α (secondary impregnation step), and the support body is then dried (secondary support step). In this method, by first supporting the auxiliary active metal α on the porous carrier, and subsequently supporting the hydrogenation active metal α on the porous carrier, the catalyst metal α is more highly dispersed to further increase the CO conversion and the alcohol selectivity.

The primary support step can be carried out, for example, by a method in which the porous carrier impregnated with the primary impregnating solution is dried (primary drying operation), and the porous carrier is then heated and baked at an arbitrary temperature (primary baking operation).

There are no particular limitations on the drying method used in the primary drying operation, and examples thereof include a method in which the porous carrier impregnated with the primary impregnating solution is heated at an arbitrary temperature. The heating temperature used in the primary drying operation may be any temperature at which the solvent of the primary impregnating solution can be evaporated, and when the solvent is water, the heating temperature is typically within a range from 80 to 120° C. The heating temperature in the primary baking operation is, for example, within a range from 300 to 600° C. By performing the primary baking operation, those components contained within the raw material compounds for the auxiliary active metal that do not contribute to the catalytic reaction can be satisfactorily volatilized, thereby further enhancing the catalytic activity.

The secondary support step can be carried out, for example, by a method in which the primary support body impregnated with the secondary impregnating solution is dried (secondary drying operation), and the support body is then heated and baked at an arbitrary temperature (secondary baking operation).

There are no particular limitations on the drying method used in the secondary drying operation, and examples thereof include a method in which the primary support body impregnated with the secondary impregnating solution is heated at an arbitrary temperature. The heating temperature used in the secondary drying operation may be any temperature at which the solvent of the secondary impregnating solution can be evaporated, and when the solvent is water, the heating temperature is typically within a range of from 80 to 120° C. The heating temperature in the secondary baking operation is, for example, within a range from 300 to 600° C. By performing the secondary baking operation, those components contained within the raw material compounds for the hydrogenation active metal that do not contribute to the catalytic reaction can be satisfactorily volatilized, thereby further enhancing the catalytic activity.

The obtained catalyst particles α are subjected to a reduction treatment to activate the catalyst particles α.

The reduction treatment can be carried out, for example, by contacting the catalyst particles α with reducing gas at preferably 200 to 600° C.

With respect to the heating time during the catalyst reduction treatment, for example, the heating time is preferably 1 to 10 hours, and more preferably 2 to 5 hours.

<Catalyst Particles β>

With respect to the catalyst particles β, there is no particular limitation as long as the catalyst particles can convert an aldehyde into an alcohol, and examples thereof include catalyst particles containing copper alone or a combination of copper and a transition metal(s) other than copper, such as copper-zinc, copper-chromium or copper-zinc-chromium, and catalyst particles containing iron, rhodium-iron, rhodium-molybdenum, palladium, palladium-iron, palladium-molybdenum, iridium-iron, rhodium-iridium-iron, iridium-molybdenum, rhenium-zinc, platinum, nickel, cobalt, ruthenium, rhodium oxide, palladium oxide, platinum oxide or ruthenium oxide (hereinafter, the metal contained in the catalyst particles β is sometimes referred to as "catalyst metal β". Among these, as the catalyst metal β, it is preferred to use copper alone or a combination of copper and a transition metal(s) other than copper, and it is more preferred to use copper, copper-zinc, copper-chromium or copper-zinc-chromium.

Further, as the catalyst particles β, it is preferred to use those which can convert not only aldehydes but also carboxylic acids or esters into alcohols. By the use of such catalyst particles β, the production efficiency of an alcohol can be further improved.

The catalyst particles β may be either in the form of an aggregate of the catalyst metal β or in the form of a supported catalyst in which the catalyst metal β is supported on a carrier. It is especially preferred to use the catalyst particles β in the form of a supported catalyst. When the catalyst particles β are in the form of a supported catalyst, an aldehyde can be more efficiently converted into an alcohol.

As the carrier for the catalyst particles β, the same as those mentioned for the catalyst particles α can be used.

The amount of the catalyst metal β supported in the supported catalyst may be determined in view of the type of the catalyst metal β and the like. For example, the amount of the catalyst metal β supported in the supported catalyst is preferably 1 to 50 parts by weight, more preferably 3 to 25 parts by weight, still more preferably 4 to 20 parts by weight, and particularly preferably 5 to 15 parts by weight, relative to 100 parts by weight of the porous carrier. When the amount is below the above-mentioned lower limit, there is a danger that the content of the supported catalyst metal β is too low so that the CO conversion is lowered. When the amount exceeds the above-mentioned upper limit, there is a danger that the surface of the porous carrier is excessively covered with the catalyst metal β so that the activity of the catalyst is lowered.

As the catalyst particles β, it is preferred to use a catalyst in which copper alone or a combination of copper with a transition metal(s) other than copper is supported on a carrier (hereinafter, sometimes referred to as "copper-type supported catalyst").

As the copper-type supported catalyst, those represented by the following formula (II) is preferred.

$$eE\cdot fF \qquad\qquad (II)$$

wherein E represents copper, F represents a transition metal other than copper, e and f represent molar ratios, and e+f=1.

In formula (II), F preferably represents zinc or chromium. As F in formula (II), a single type of metal may be used, or two or more types of metals may be used in combination.

In formula (II), e is preferably 0.5 to 0.9, more preferably 0.5 to 0.7, and still more preferably 0.5 to 0.6. When the value of e is below the above-mentioned lower limit, the content of copper is too low and, hence, there is a danger that the efficiency of converting an aldehyde into an alcohol is lowered. When the value of e exceeds the above-mentioned upper limit, the content of component F is too low and, hence, there is a danger that the efficiency of converting an aldehyde, a carboxylic acid or an ester into an alcohol is lowered.

In formula (II), f is preferably 0.1 to 0.5, more preferably 0.3 to 0.5, and still more preferably 0.4 to 0.5. When the value of f is below the above-mentioned lower limit, the content of component F is too low and, hence, there is a danger that the efficiency of converting an aldehyde, a carboxylic acid or an ester into an alcohol is lowered. When the value of f exceeds the above-mentioned upper limit, the content of copper is too low and, hence, there is a danger that the efficiency of converting an aldehyde into an alcohol is lowered.

As a preferable combination of the catalyst particles α and the catalyst particles β, there can be mentioned a combination of catalyst particles α containing rhodium without containing copper, and catalyst particles β containing copper without containing rhodium.

With respect to the average particle diameter of the catalyst particles β, the same as mentioned above for the catalyst particles α can be mentioned.

The average particle diameter of the catalyst particles β may be the same as or different from the average particle diameter of the catalyst particles α. However, for preventing spontaneous classification of the catalyst into the catalyst particles α and the catalyst particles β, it is preferable that the ratio represented by [average particle diameter of catalyst particles α]/[average particle diameter of catalyst particles β] is 0.5 to 2.

The specific gravity of the catalyst particles β may be the same as or different from the specific gravity of the catalyst particles α. However, for preventing spontaneous separation of the catalyst particles α from the catalyst particles β, it is preferable that the ratio represented by [specific gravity of catalyst particles α]/[specific gravity of catalyst particles β] is 0.5 to 2.

The content of the catalyst particles β in the synthesis catalyst may be determined in view of the performance of the catalyst particles β and the like and, for example, can be appropriately determined within the range of 9 to 91% by mass.

The synthesis catalyst may contain one type of the catalyst particles β or two or more types of the catalyst particles β.

The mass ratio in terms of catalyst particles β/catalyst particles α (hereinafter, β/α mass ratio) is, for example, preferably 1 or more, more preferably more than 1, still more preferably more than 1 and 10 or less, and particularly preferably 2.5 to 5. When the β/α mass ratio is below the above-mentioned lower limit, there is a danger that the CO conversion is lowered at an early stage. When the β/α mass ratio exceeds the above-mentioned upper limit, there is a danger that the production of an alcohol per unit mass of the synthesis catalyst is lowered, thereby lowering the production efficiency.

In the catalyst of the present invention, it is preferred that the volume ratio in terms of [volume of catalyst particles β prior to mixing]/[volume of catalyst particles α prior to mixing] (hereinafter, β/α volume ratio) is preferably 1 or more, more preferably more than 1, still more preferably more than 1 and 15 or less, and particularly preferably 2.5 to 7. When the β/α volume ratio is below the above-mentioned lower limit, there is a danger that the CO conversion is lowered at an early stage. When the β/α volume ratio exceeds the above-mentioned upper limit, there is a danger that the production of an alcohol per unit mass of the synthesis catalyst is lowered, thereby lowering the production efficiency. Here, each of [volume of catalyst particles β prior to mixing] and [volume of catalyst particles α prior to mixing] is an apparent volume prior to mixing.

As examples of a method for producing the catalyst particles β, the same as mentioned above for the production of the catalyst particles α can be mentioned.

The obtained catalyst particles β are subjected to a reduction treatment to activate the catalyst particles β.

The reduction treatment can be carried out, for example, by contacting the catalyst particles β with reducing gas at preferably 200 to 600° C.

With respect to the heating time during the catalyst reduction treatment, for example, the heating time is preferably 1 to 10 hours, and more preferably 2 to 5 hours.

<Other Catalyst Particles>

The synthesis catalyst may also contain other catalyst particles than the catalyst particles α and the catalyst particles β; however, from the viewpoint of suppressing side reactions and preventing the lowering of the alcohol production efficiency, it is preferable that the synthesis catalyst consists substantially only of the catalyst particles α and the catalyst particles β. Here, the expression "consists substantially only of the catalyst particles α and the catalyst particles β" means that the synthesis catalyst does not at all contain any catalyst particles other than the catalyst particles α and the catalyst particles β or that the synthesis catalyst contains catalyst particles other than the catalyst particles α and the catalyst particles β in such an amount as would not affect the effect of the present invention.

As to the method for producing the synthesis catalyst, the method comprises mixing the catalyst particles α and the catalyst particles β. Specific method for mixing the catalyst particles α and the catalyst particles β is not particularly limited, and examples thereof include a method in which the catalyst particles α and the catalyst particles β are mixed by a powder mixer or the like.

(Alcohol Production Apparatus)

The alcohol production apparatus of the present invention (hereinafter, sometimes referred to simply as "production apparatus") comprises: a reaction tube filled with the synthesis catalyst; a supply means for supplying the gaseous mixture to the reaction tube; and a withdrawal means for withdrawing a reaction product from the reaction tube.

Figure 1:
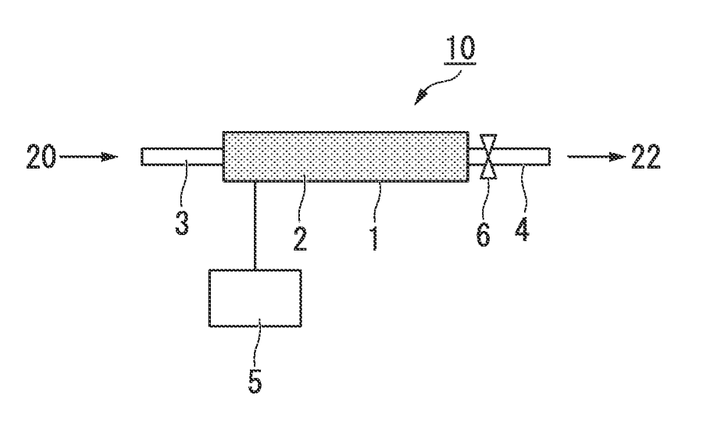
FIG. 1 is a schematic view of the alcohol production apparatus according to an embodiment of the present invention.

Explanations are made below with respect to an example of the production apparatus of the present invention referring to FIG. 1. FIG. 1 is a schematic view of the production apparatus 10 according to an embodiment of the present invention. The production apparatus 10 shown in FIG. 1 has a reaction tube 1 which is filled with the synthesis catalyst and has formed therein a reaction bed 2; a supply tube 3 connected with the reaction tube 1; a withdrawal tube 4 connected with the reaction tube 1; a temperature control part 5 connected with the reaction tube 1; and a pressure control part 6 provided at the withdrawal tube 4.

The synthesis reaction bed 2 may be either one charged only with the synthesis catalyst or one charged with a mixture of the synthesis catalyst and a diluent. The diluent is used for preventing excessive heat generation of the synthesis catalyst during the alcohol production, and examples thereof include those mentioned above for the catalyst particles α, crystal sand, alumina balls and the like.

When the diluent is filled into the reaction bed 2, the weight ratio in terms of diluent/synthesis catalyst may be determined in view of the types of the diluent and the catalyst and is, for example, preferably 0.5 to 5.

However, in the present invention, the catalyst particles β function as a diluent for the catalyst particles α; therefore, it is preferable that the reaction bed 2 is filled with only the synthesis catalyst. When a diluent is not used, it becomes possible to increase the production amount of an alcohol per unit volume of the reaction bed 2 and to downsize the production apparatus 10.

The reaction tube 1 is preferred to be made of a material which is inert to the gaseous mixture and the synthesized oxygenate and is preferred to have a shape such that the reaction tube 1 can withstand a heating at around 100 to 500° C. and a pressure of around 10 MPa.

As a specific example of the reaction tube 1, there can be mentioned an approximately cylindrical part made of a stainless steel.

The supply tube 3 is a means for supplying a gaseous mixture to the reaction tube 1, and may be, for example, a pipe made of a stainless steel etc.

The withdrawal tube 4 is a means for withdrawing a synthesized gas (product) containing an alcohol synthesized in the reaction bed 2, and may be, for example, a pipe made of a stainless steel etc.

With respect to the temperature control part 5, there is no particular limitation as long as it can control the temperature of the reaction bed 2 in the reaction tube 1 to a desired value, and examples of the temperature control part 5 include an electric furnace and the like.

With respect to the pressure control part 6, there is no particular limitation as long as it can control the internal pressure of the reaction tube 1 to a desired value, and examples of the pressure control part 6 include a known pressure valve or the like.

The production apparatus 10 may be equipped with a known device such as a gas flow rate controller (e.g., mass flow controller) or the like which adjusts a flow rate of the gas.

(Alcohol Production Method)

The alcohol production method of the present invention comprises contacting a gaseous mixture with a synthesis catalyst. Explanations are made below with respect to an example of the alcohol production method referring to FIG. 1.

First, the temperature and pressure in the reaction tube 1 are adjusted to predetermined values, and the gaseous mixture 20 is introduced into the reaction tube 1 through the supply tube 3.

There is no limitation on the gaseous mixture 20 as long as it contains hydrogen and carbon monoxide. For example, the gaseous mixture 20 may be a natural gas or a coal-derived gas, or may be a biomass gas obtained by gasification of a biomass, or gas (hereinafter, sometimes referred to as "recycle gas") obtained by gasification of organic wastes such as waste plastics, waste papers or waste clothes. A biomass gas and a recycle gas can be obtained by any of the conventional methods such as a method in which a pulverized biomass or organic waste is heated in water vapor while heating at, for example, 800 to 1,000° C.

When a biomass gas or a recycle gas is used as the gaseous mixture 20, before being introduced into the reaction tube 1, the gaseous mixture 20 may be subjected to a gas purification treatment for removing impurities, such as a tar content, a sulfur content, a nitrogen content, a chlorine content, and moisture. Examples of methods that may be employed for the gas purification treatment include any of the methods known within the technical field, including wet methods and dry methods. Examples of the wet methods include the sodium hydroxide method, ammonia absorption method, lime-gypsum method and magnesium hydroxide method, whereas examples of the dry methods include activated carbon adsorption methods such as the pressure swing adsorption (PSA) method, and an electron beam method.

The gaseous mixture 20 is preferably a gas containing hydrogen and carbon monoxide as the main components, namely a gas in which the total amount of hydrogen and carbon monoxide within the gaseous mixture 20 is preferably at least 50% by volume, more preferably at least 80% by volume, still more preferably at least 90% by volume, and may be even 100% by volume. As the content of hydrogen and carbon monoxide increases, the efficiency of alcohol production can be improved further.

In the gaseous mixture 20, the volume ratio represented by hydrogen/carbon monoxide (hereafter also referred to as the $H_2/CO$ ratio) is preferably within a range from 1/5 to 5/1, more preferably from 1/2 to 3/1, and still more preferably from 1/1 to 2.5/1. When the $H_2/CO$ ratio is within the above-mentioned range, the stoichiometric balance is maintained within an appropriate range during the catalytic reaction producing an oxygenate, thereby enabling more efficient production of an alcohol.

Besides the hydrogen and carbon monoxide, the gaseous mixture 20 may also contain methane, ethane, ethylene, nitrogen, carbon dioxide, water and the like.

The temperature at which the gaseous mixture 20 and the catalyst are to be brought into contact (reaction temperature), namely the temperature inside the reaction tube 1, is preferably within a range from 150 to 450° C., more preferably from 200 to 400° C., and still more preferably from 250 to 350° C. When the reaction temperature is not below the above-mentioned lower limit, the rate of catalytic reaction can be sufficiently increased to enable more efficient production of an alcohol. When the temperature is not greater than the upper limit, the alcohol synthesis reaction becomes the predominant reaction, and the alcohol can be produced more efficiently.

The pressure under which the gaseous mixture 20 and the catalyst are to be brought into contact (reaction pressure), namely the pressure inside the reaction tube 1, is preferably within a range from 0.5 to 10 MPa, more preferably from 1 to 7.5 MPa, and still more preferably from 2 to 5 MPa. When the reaction pressure is not below the above-mentioned lower limit, the rate of catalytic reaction can be sufficiently increased to enable more efficient production of an alcohol. When the temperature is not greater than the upper limit, the alcohol synthesis reaction becomes the predominant reaction, and the alcohol can be produced more efficiently.

The introduced gaseous mixture 20 flows through the reaction tube while contacting with the catalyst particles α in the reaction bed 2, and a portion of the gaseous mixture is converted to the oxygenates including alcohols such as ethanol, and by-products such as aldehydes, carboxylic acids and esters via the catalytic reactions such as those represented by the formulae (1) to (3) shown below. Of the by-products, an aldehyde such as acetaldehyde is rapidly converted to an alcohol (formula (4) below).

$$2H_2 + 2CO \rightarrow CH_3COOH \quad (1)$$

$$3H_2 + 2CO \rightarrow CH_3CHO + H_2O \quad (2)$$

$$4H_2 + 2CO \rightarrow CH_3CH_2OH + H_2O \quad (3)$$

$$H_2 + CH_3CHO \rightarrow CH_3CH_2OH \quad (4)$$

Then, the resultant synthesis gas 22 containing alcohols is discharged from the discharge tube 4. There is no particular limitation on the synthesis gas 22 as long as it contains an alcohol, and the synthesized gas 22 may further contain, for example, oxygenates other than alcohols, hydrocarbons such as methane, and the like.

With respect to the synthesis gas 22, the selectivity for alcohols is preferably 40 mol % or more, and more preferably 50 mol % or more. When the selectivity for alcohols is not less than the aforementioned lower limit, it becomes possible to simplify or omit some steps such as a step for removing compounds other than alcohols.

The supply rate of the gaseous mixture 20 is, for example, preferably 10 to 100,000 L/L-catalyst/h, more preferably 1,000 to 50,000 L/L-catalyst/h, and still more preferably 3,000 to 20,000 L/L-catalyst/h in terms of the space velocity of the gaseous mixture (calculated as a standard state value thereof) in the reaction bed 2 (the value obtained by dividing the gas supply volume per unit of time by the amount of the catalyst (in terms of volume)). The space velocity is adjusted as appropriate, with due consideration of the reaction pressure, the reaction temperature and the composition of the gaseous mixture as the raw material.

If necessary, the synthesis gas 22 discharged from the discharge tube 4 may be processed in a gas-liquid separator or the like to separate the alcohols from the unreacted gaseous mixture 20 and the by-products.

In the present embodiment, the gaseous mixture is brought into contact with the reaction bed 2 that is a fixed bed, but the synthesis catalyst may also be provided in other form than a fixed bed, for example, in the form of a fluidized bed or a moving bed, with which the gaseous mixture is contacted.

In the present invention, the by-products contained in the obtained synthesis gas 22 may, if necessary, be separated into respective components by distillation or the like.

Further, in the present invention, a step of hydrogenating products other than alcohols and converting these products to alcohols (an alcoholification step) may also be provided. The alcoholification step can be carried out, for example, by a method in which oxygenates including acetaldehyde, acetic acid, etc. are contacted with a hydrogenation catalyst to convert the oxygenates into alcohols.

As the hydrogenation catalyst, any of those known in this technical field can be used, and examples thereof include the same as those mentioned for the catalyst particles β.

By the catalyst of the present invention which is a mixture of the catalyst particles α and the catalyst particles β, an alcohol can be produced with higher production efficiency over a long period of time.

The reason for this is not elucidated but is considered to be as follows.

In the production of an oxygenate form the gaseous mixture, the synthesis catalyst catalyzes reactions producing an alcohol as the main product and an aldehyde as the by-product. This aldehyde causes the activity of the synthesis catalyst to be lowered at an early stage.

In the case of the synthesis catalyst of the present invention, it is considered that an aldehyde (e.g., acetaldehyde) by-produced in the synthesis of an alcohol by the action of the catalyst particles α is rapidly converted into an alcohol (e.g., ethanol) by the action of the catalyst particles β, thereby enabling the suppression of the lowering of the activity of the catalyst particles α.

EXAMPLES

Hereinbelow, the present invention will be described with reference to the examples which, however, should not be construed as limiting the present invention.

Production Example 1

Production of Catalyst Particles α

First, 0.61 mL of an aqueous solution containing 0.0123 g of an ammonium titanium lactate salt $(Ti(OH)_2[OCH(CH_3)COO^-]_2(NH_4^+)_2)$ was added dropwise to 1.0 g of a spherical silica gel (particle size: 1 to 2 mm, specific surface area: 430 m$^2$/g; average pore diameter: 5.7 nm, total pore volume: 0.61 mL/g) to impregnate the spherical silica gel. The resultant was dried at 110° C. for 3 hours, followed by calcination at 450° C. for 3 hours, thereby obtaining a primary supported body. Subsequently, 0.61 mL of an aqueous solution containing 0.0768 g of rhodium chloride trihydrate ($RhCl_3.3H_2O$), 0.048 g of lithium chloride monohydrate ($LiCl.H_2O$), and 0.0433 g of manganese chloride tetrahydrate ($MnCl_2.4H_2O$) was added dropwise to the primary supported body to impregnate the primary supported body, and the resultant was dried at 110° C. for 3 hours and then baked at 400° C. for 3 hours to obtain catalyst particles α. With respect to the obtained catalyst particles α, it was found that rhodium, manganese, lithium and titanium were contained as the catalyst metals α, and that the ratio of supported rhodium=3% by mass/SiO, and Rh:Mn:Li:Ti=1.00:0.750:0.275:0.143 (molar ratio).

Production Example 2

Production of Catalyst Particles β-1

First, 0.95 mL of an aqueous solution containing 0.344 g of copper nitrate trihydrate ($Cu(NO_3)_2.3H_2O$) and 0.412 g of zinc nitrate hexahydrate ($Zn(NO_3)_3.6H_2O$) was added dropwise to 1.0 g of a spherical silica gel (particle size: 1 to 2 mm, specific surface area: 315 m$_2$/g; average pore diameter: 10 nm, total pore volume: 0.95 mL/g) to impregnate the spherical silica gel. The resultant was dried at 110° C. for 3 hours, followed by calcination at 400° C. for 3 hours, thereby obtaining catalyst particles β-1 as the catalyst particles β. With respect to the obtained catalyst particles β-1, it was found that copper and zinc were contained as the catalyst metals β, and that the ratio of supported copper=9% by mass/SiO, and Cu:Zn=1.00:0.97 (molar ratio).

Production Example 3

Production of Catalyst Particles β-2

The same procedure as in Production Example 2 was repeated except that the amount of copper nitrate trihydrate ($Cu(NO_3)_2.3H_2O$) was changed to 0.190 g and the amount of zinc nitrate hexahydrate ($Zn(NO_3)_3.6H_2O$) was changed to 0.227 g, to thereby obtain catalyst particles β-2 as the catalyst particles β. With respect to the obtained catalyst particles β-2, it was found that copper and zinc were contained as the catalyst metals β, and that the ratio of supported copper=5% by mass/SiO, and Cu:Zn=1.00:0.97 (molar ratio).

Production Example 4

Production of Comparative Synthesis Catalyst (Comparative Catalyst)

First, 0.61 mL of an aqueous solution containing 0.115 g of copper nitrate trihydrate ($Cu(NO_3)_2.3H_2O$) and 0.137 g of zinc nitrate hexahydrate ($Zn(NO_3)_3.6H_2O$) was added dropwise to 1.045 g of the catalyst particles α obtained in Production Example 1. The resultant was dried at 110° C. for 3 hours, followed by calcination at 400° C. for 3 hours, thereby obtaining a comparative catalyst. With respect to the obtained comparative catalyst, it was found that the ratio of supported rhodium=3% by mass/SiO$_2$, and Rh:Mn:Li:Ti:Cu:Zn=1.00:0.750:0.275:0.143:1.63:1.58 (molar ratio).

Example 1

0.5 g of the catalyst particles α obtained in Production Example 1 and 0.5 g of the catalyst particles β-1 obtained in Production Example 2 were mixed together to obtain a synthesis catalyst. The thus obtained synthesis catalyst and 3.0 g of the same spherical silica gel having a particle size of 1 to 2 mm (diluent) as used in Production Example 1 were mixed. The resultant was charged into a cylindrical stainless steel reaction tube having an inner diameter of 10.7 mm and a length of 40 cm to form a reaction bed, thereby obtaining the same alcohol production apparatus as the alcohol production apparatus 10 shown in FIG. 1.

The catalyst was subjected to a reduction treatment by heating at 320° C. for 2 hours while flowing a reduction gas (hydrogen content: 30% by volume, nitrogen content: 70% by volume) under normal pressure through the reaction bed at 6,000 L/L-catalyst/h.

Then, an alcohol (ethanol) was produced in the following manner.

The reaction bed was cooled to 260° C., followed by flowing a gaseous mixture (H$_2$/CO ratio=2) at 9,000 L/L-catalyst/h and increasing the reaction pressure to 0.9 MPa. The, the reaction temperature was increased to 280° C. at a rate of 1° C./min., and the time when the temperature became stable was taken as the time of initiation of the reaction. The synthesized gas was recovered at 1 hour after the initiation of the reaction and analyzed by gas chromatography. From the obtained data, the CO conversion (mol %) and the selectivity for the product (mol %) were calculated. The synthesized gas was recovered at 24 hour after the initiation of the reaction and analyzed by gas chromatography. From the obtained data, the CO conversion and the selectivity for the product were calculated. The activity maintenance ratio was calculated by the formula (10) shown below. The results are shown in Table 1.

In the table, the form of reaction bed in this Example is indicated as "mixed type".

Further, in the table, the mass ratio β/α represents a mass ratio of the catalyst particles β-1 or β-2 to the catalyst particles α in the synthesis catalyst, and the volume ratio β/α represents a volume ratio of the catalyst particles β-1 or β-2 to the catalyst particles α in the synthesis catalyst.

Activity maintenance ratio (%)=[CO conversion after 24 hours]÷[CO conversion after 1 hour]×100    (10)

Example 2

An alcohol was produced in the same manner as in Example 1 except that a mixture of 0.5 g of the catalyst particles α and 1.0 g of the catalyst particles β-1 was used as the synthesis catalyst, and the amount of the diluent was changed to 2.5 g. The CO conversion, the selectivity for the product and the activity maintenance ratio were measured in the same manner as in Example 1, the results of which are shown in Table 1.

In the table, the form of reaction bed in this Example is indicated as "mixed type".

Example 3

An alcohol was produced in the same manner as in Example 1 except that a mixture of 0.5 g of the catalyst particles α and 1.5 g of the catalyst particles β-1 was used as the synthesis catalyst, and the amount of the diluent was changed to 2.0 g. The CO conversion, the selectivity for the product and the activity maintenance ratio were measured in the same manner as in Example 1, the results of which are shown in Table 1.

In the table, the form of reaction bed in this Example is indicated as "mixed type".

Example 4

An alcohol was produced in the same manner as in Example 1 except that a mixture of 0.5 g of the catalyst particles α and 1.5 g of the catalyst particles β-1 was used as the synthesis catalyst, and the diluent was not added. The CO conversion, the selectivity of the product and the activity maintenance ratio were measured in the same manner as in Example 1, the results of which are shown in Table 1.

In the table, the form of reaction bed in this Example is indicated as "mixed type".

Example 5

An alcohol was produced in the same manner as in Example 4 except that 1.5 g of the catalyst particles β-2 was used instead of the catalyst particles β-1, and the CO conversion, the selectivity for the product and the activity maintenance ratio were measured. The results are shown in Table 1.

In the table, the form of reaction bed in this Example is indicated as "mixed type".

Example 6

An alcohol was produced in the same manner as in Example 5 except that the amount of the catalyst particles β-2 was changed to 3.0 g, and the CO conversion, the selectivity for the product and the activity maintenance ratio were measured. The results are shown in Table 1.

In the table, the form of reaction bed in this Example is indicated as "mixed type".

Example 7

An alcohol was produced in the same manner as in Example 4 except that a synthesis catalyst prepared by mixing 0.5 g of the catalyst particles α and 1.5 g of the catalyst particles β-1 was used as an upper layer of the reaction bed while 1.0 g of the catalyst particles β-1 were used as a lower layer of the reaction bed, and the CO conversion, the selectivity for the product and the activity maintenance ratio were measured. The results are shown in Table 1.

In the table, the form of reaction bed in this Example is indicated as "mixed double-layer type".

Example 8

An alcohol was produced in the same manner as in Example 4 except that a synthesis catalyst prepared by mixing 0.5 g of the catalyst particles α and 1.5 g of the catalyst particles β-2 was used as an upper layer of the reaction bed while 1.0 g of the catalyst particles β-2 were used as a lower layer of the reaction bed, and the CO conversion, the selectivity for the product and the activity maintenance ratio were measured. The results are shown in Table 1.

In the table, the form of reaction bed in this Example is indicated as "mixed double-layer type".

Comparative Example 1

An alcohol was produced in the same manner as in Example 1 except that a mixture 0.5 g of the catalyst particles α and 1.0 g of the spherical silica gel (diluent) was used as an upper layer of the reaction bed while a mixture of 1.5 g of the catalyst particles β-1 and 1.0 g of the spherical silica gel (diluent) was used as a lower layer of the reaction bed, wherein a silicon oxide layer having a height of 1 cm was provided between the upper layer and the lower layer. The CO conversion, the selectivity for the product and the activity maintenance ratio were measured in the same manner as in Example 1, the results of which are shown in Table 1.

In the table, the form of reaction bed in this Example is indicated as "double-layer type".

Comparative Example 2

An alcohol was produced in the same manner as in Example 1 except that a mixture of 0.5 g of the catalyst particles α and 1.0 g of the spherical silica gel (diluent) was used as the reaction bed. The CO conversion, the selectivity for the product and the activity maintenance ratio were measured in the same manner as in Example 1, the results of which are shown in Table 1.

In the table, the form of reaction bed in this Example is indicated as "single type".

Comparative Example 3

An alcohol was produced in the same manner as in Example 1 except that a mixture of 0.5 g of the comparative catalyst obtained in Production Example 4 and 1.0 g of the spherical silica gel as a diluent was used as the reaction bed. The CO conversion, the selectivity for the product and the activity maintenance ratio were measured in the same manner as in Example 1, the results of which are shown in Table 1.

In the table, the form of reaction bed in this Example is indicated as "single type".

In this Comparative Example, the CO conversion after 1 hour was markedly low and, hence, the CO conversion after 24 hours and the selectivity for the product were not measured.

As shown in Table 1, in Examples 1 to 8 according to the present invention, the CO conversion after 24 hours is 65 mol % or more and the activity maintenance ratio is 62% or more.

From the comparison between the results of Examples 1 to 3, it is found that the higher the volume ratio β/α, the higher are the CO conversion after 24 hours and the activity maintenance ratio.

From the comparison between the results of Examples 3 and 4, it is found that, in Example 4 where the diluent was not used, the selectivity for acetaldehyde was higher than Example 3 where the diluent was used, but the activity maintenance ratio was 62%. From these results, it has been found that the local temperature increase and the reaction runaway in the reaction bed can be suppressed without a diluent.

TABLE 1

| | | | Examples | | | | | |
|---|---|---|---|---|---|---|---|---|
| | | | 1 | 2 | 3 | 4 | 5 | 6 |
| Specification | Form of reaction bed | | Mixed type | Mixed type | Mixed type | Mixed type | Mixed type | Mixed type |
| | β/α mass ratio | | 1 | 2 | 3 | 3 | 3 | 6 |
| | β/α volume ratio | | 1.3 | 2.7 | 4.0 | 4.0 | 4.2 | 8.4 |
| | Diluent | | Contained | Contained | Contained | Not contained | Not contained | Not contained |
| Results | CO conversion (mol %) | After 1 hour | 10.5 | 10.3 | 10.8 | 11.0 | 9.6 | 9.8 |
| | | After 24 hours | 6.5 | 6.6 | 7.2 | 6.8 | 6.8 | 6.6 |
| | Activity maintenance ratio | | 62 | 64 | 67 | 62 | 71 | 67 |
| | Molar ratio (mol %) | After 1 hour Ethanol | 40.0 | 48.6 | 55.8 | 51.3 | 56.9 | 58.4 |
| | | Acetaldehyde | 15.4 | 7.6 | 1.5 | 4.0 | 3.6 | 2.3 |
| | | Ethyl acetate | 1.6 | 0.8 | 0.6 | 0.8 | 0.7 | 0.4 |
| | | Methane | 31.5 | 30.4 | 29.4 | 33.2 | 30.8 | 30.0 |
| | | C2-C4 hydrocarbons | 11.3 | 12.1 | 12.7 | 10.3 | 7.6 | 8.2 |
| | | Others | 0.2 | 0.5 | 0.0 | 0.4 | 0.4 | 0.7 |
| | | After 24 hours Ethanol | 45.2 | 49.0 | 54.5 | 52.3 | 55.6 | 57.3 |
| | | Acetaldehyde | 10.8 | 7.3 | 1.4 | 3.0 | 3.0 | 2.0 |
| | | Ethyl acetate | 1.4 | 0.7 | 1.0 | 0.8 | 0.4 | 0.3 |
| | | Methane | 30.4 | 29.8 | 29.8 | 33.0 | 32.4 | 31.4 |
| | | C2-C4 hydrocarbons | 11.4 | 11.9 | 12.4 | 10.6 | 8.2 | 8.4 |
| | | Others | 0.8 | 1.3 | 0.9 | 0.3 | 0.4 | 0.6 |

| | | | Examples | | Comparative Examples | | |
|---|---|---|---|---|---|---|---|
| | | | 7 | 8 | 1 | 2 | 3 |
| Specification | Form of reaction bed | | Mixed double-layer type | Mixed double-layer type | Double-layer type | Single type | Single type |
| | β/α mass ratio | | 3 | 3 | 3 | — | — |
| | β/α volume ratio | | 4.0 | 4.2 | 4.0 | — | — |
| | Diluent | | Not contained | Not contained | Contained | Contained | Contained |
| Results | CO conversion (mol %) | After 1 hour | 10.8 | 9.6 | 10.3 | 10.6 | 2.3 |
| | | After 24 hours | 6.8 | 6.8 | 5.4 | 5.7 | — |
| | Activity maintenance ratio | | 63 | 71 | 52 | 54 | — |
| | Molar ratio (mol %) | After 1 hour Ethanol | 54.3 | 62.4 | 54.9 | 20.8 | 24.3 |
| | | Acetaldehyde | 2.4 | 0.9 | 0.7 | 31.7 | 1.5 |
| | | Ethyl acetate | 0.4 | 0.0 | 0.6 | 3.1 | 0.3 |
| | | Methane | 31.5 | 28.8 | 30.7 | 31.9 | 52.9 |
| | | C2-C4 hydrocarbons | 11.0 | 7.5 | 12.9 | 11.3 | 19.1 |
| | | Others | 0.4 | 0.4 | 0.2 | 1.2 | 1.9 |
| | | After 24 hours Ethanol | 54.5 | 60.4 | 55.6 | 23.4 | — |
| | | Acetaldehyde | 2.0 | 1.1 | 0.9 | 31.2 | — |
| | | Ethyl acetate | 0.5 | 0.0 | 0.5 | 1.1 | — |
| | | Methane | 31.8 | 30.4 | 0.7 | 32.3 | — |
| | | C2-C4 hydrocarbons | 10.8 | 7.5 | 10.3 | 10.6 | — |
| | | Others | 0.4 | 0.6 | 2.0 | 1.4 | — |

From the comparison between the results of Examples 4 and 5, it is found that, in Example 5 where the catalyst particles β-2 were used, the selectivity for ethanol is high, the selectivity for C2-C4 hydrocarbons is low and the activity maintenance ratio is high as compared to Example 4 where the catalyst particles β-1 were used.

From the comparison between the results of Examples 5 and 6, it is found that, in Example 6 where the amount of catalyst particles β-2 was increased, the selectivity for ethanol is high and the selectivity for acetaldehyde is low as compared to Example 5.

From the comparison between the results of Examples 4 and 7 and between the results of Examples 5 and 8, it is found that, when a reaction bed of the catalyst particles β is provided downstream of a reaction bed of a mixture of the catalyst particles α and the catalyst particles β, the selectivity for ethanol is further increased while the selectivities for acetaldehyde and ethyl acetate are further decreased.

By contrast, in Comparative Example 1 where the reaction bed was a double-layer type formed of a layer of the catalyst particles α and a layer of the catalyst particles β, and Comparative Example 2 where the reaction bed was formed only of the catalyst particles α, the CO conversion after 24 hours is 5.7 mol % or less and the activity maintenance ratio is 54% or less.

Further, with respect to the catalyst of Comparative Example 3 in which both of the catalyst metal α of the catalyst particles α of Production Example 1 and the catalyst metal β of the catalyst particles β-1 of Production Example 2 were supported together on the carrier, the initial CO conversion was 2.3 mol %.

From these results, it has been found that, by application of the present invention, an alcohol can be produced with higher production efficiency over a long period of time.

DESCRIPTION OF THE REFERENCE SIGNS

1 Reaction tube
2 Reaction bed
3 Supply pipe
4 Withdrawal pipe
5 Temperature control unit
6 Pressure control unit
10 Production apparatus
20 Gaseous mixture
22 Synthesis gas

The invention claimed is:

1. A catalyst for synthesizing an alcohol from a gaseous mixture comprising hydrogen and carbon monoxide,
the catalyst being a mixture of catalyst particles α which convert carbon monoxide into an oxygenate, and catalyst particles β which convert an aldehyde into an alcohol, each of the catalyst particles α and the catalyst particles β being in the form of a supported catalyst, and
a volume ratio in terms of [catalyst particles β prior to mixing]/[catalyst particles α prior to mixing] being 2.5 to 7.

2. The catalyst for synthesizing an alcohol according to claim 1, wherein the catalyst particles α comprise rhodium and the catalyst particles β comprise copper.

3. A method for producing an alcohol, comprising contacting a gaseous mixture comprising hydrogen and carbon monoxide with the catalyst for synthesizing an alcohol according to claim 1.

4. A method for producing an alcohol, comprising contacting a gaseous mixture comprising hydrogen and carbon monoxide with the catalyst for synthesizing an alcohol according to claim 2.

5. The catalyst for synthesizing an alcohol according to claim 1, wherein each of the catalyst particles α and the catalyst particles β independently comprise a catalyst metal supported on a porous carrier selected from the group consisting of silica, zirconia, titania, magnesia, alumina, activated carbon, and zeolite.

* * * * *